United States Patent
Denq et al.

(10) Patent No.: US 7,426,851 B2
(45) Date of Patent: Sep. 23, 2008

(54) GAS SENSOR UNIT AND METHOD OF FORMING THE SAME

(75) Inventors: Bar-Long Denq, Taipei (TW); Chien-Chun Wu, Taipei (TW)

(73) Assignee: Compal Electronics, Inc., Taipei (TW)

( * ) Notice: Subject to any disclaimer, the term of this patent is extended or adjusted under 35 U.S.C. 154(b) by 0 days.

(21) Appl. No.: 11/682,321

(22) Filed: Mar. 6, 2007

(65) Prior Publication Data
US 2007/0266770 A1   Nov. 22, 2007

(30) Foreign Application Priority Data
May 22, 2006   (TW) ............... 95118068 A

(51) Int. Cl.
G01N 27/12   (2006.01)
(52) U.S. Cl. ...................... 73/31.05; 73/23.2
(58) Field of Classification Search ............ 73/23.2, 73/31.05
See application file for complete search history.

(56) References Cited

U.S. PATENT DOCUMENTS 4,604,427 A * 8/1986 Roberts et al. .............. 525/185
7,008,565 B2 * 3/2006 Osherov et al. ............. 252/511
2002/0182739 A1 * 12/2002 Sadik et al. ................. 436/106

OTHER PUBLICATIONS

Brady, S. et al., "Inherently Conducting Polymer Modified Polyurethane Smart Foam for Pressure Sensing", Sensors and Actuators A, vol. 119, (2005), pp. 398-404.*

Wojkiewicz, J.L. et al., "Intrinsically Conductivie Nanocomposites: High Performance Electromagnetic Shielding Materials" IEEE, (2005), pp. 58-61.*

Njugana, J. et al., "Review Recent Developments in Polyurethane-Based Conducting Composites", Journal of Materials Science, vol. 39, (2004), pp. 4081-4094.*

Ruckenstein, E. et al., "Polypyrrole Conductive Composites Prepared by Coprecipitation", Polymer, vol. 32 (1991), pp. 1230-1235 (Abstract Only).*

* cited by examiner

*Primary Examiner*—Daniel S Larkin
(74) *Attorney, Agent, or Firm*—Jianq Chyun IP Office

(57) ABSTRACT

A gas sensor unit includes a conductive polymer and an absorbent for absorbing gas molecules. The conductive polymer is polyaniline (PAN) and the absorbent is polyurethane (PU). The content of the conductive polymer is 25-55 wt % and the content of the absorbent is 45-75 wt %.

15 Claims, 6 Drawing Sheets

GAS SENSOR UNIT AND METHOD OF FORMING THE SAME

CROSS-REFERENCE TO RELATED APPLICATION

This application claims the priority benefit of Taiwan application serial no. 95118068, filed on May 22, 2006. All disclosure of the Taiwan application is incorporated herein by reference.

BACKGROUND OF THE INVENTION

1. Field of the Invention

The present invention relates to a gas sensor unit and a method of forming the same. More particularly, the present invention relates to a low cost and highly sensitive gas sensor unit, and a method of forming the same.

2. Description of Related Art

In order to prevent the leakage of various toxic, flammable, explosive, or dangerous gases used or produced during industrial processes, which is harmful to human beings and causes great damage to the environment, recently, a sensor capable of detecting various gas molecules was developed and it has attracted the attention from all circles. Such gas sensor has featured high sensitivity, low cost, good selectivity, rapid response, high stability, reproducibility, and so on.

Presently, the gas sensors generally available include catalyst combustion type, metal semiconductor absorption type and conductive polymer material type, and so on. However, all the current gas sensor materials, such as in the catalyst combustion type or metal oxide absorption type gas sensor, commonly used for gases like alcohols need to be operated at high temperature, so that the detection application thereof for flammable gases are limited.

Since the conductive polymer material has a single/double alternating conjugated bond, due to the specific electron configuration thereof, the electrons can hop along the molecular chain or across the molecular chain after being oxidized or reduced, so that the material is conductive. Therefore, the material can be used to sense gas at ambient temperature.

However, in the current study concerning a gas sensor of the conductive polymer material, only polypyrrole (PPy) has been studied. Presently, PPy has no commercial application, since it is expensive and the source thereof is not readily available.

SUMMARY OF THE INVENTION

Accordingly, the present invention is directed to a gas sensor unit having the advantages of low cost and high sensitivity.

The present invention is also directed to a method of forming a low cost and highly sensitive gas sensor unit.

The present invention provides a gas sensor unit including a conductive polymer and an absorbent for absorbing gas molecules. The conductive polymer is polyaniline (PAN) and the absorbent is polyurethane (PU). The conductive polymer is 25-55 wt % of the total weight of the gas sensor unit, and the absorbent is 45-75 wt % of the total weight of the gas sensor unit.

According to a preferred embodiment of the present invention, the absorbed gas molecules include molecules of alcohols, such as methanol and ethanol.

According to a preferred embodiment of the present invention, a sensing circuit is further included for sensing the resistance of the gas sensor unit. The sensing circuit may be comprised of an alumina ceramic leaded chip carrier (CLCC).

According to a preferred embodiment of the present invention, the gas sensor unit is used to detect a gas of alcohols by absorbing/desorbing the gas molecules of the alcohols whereby the resistance of the gas sensor unit change.

The present invention provides a method of forming a gas sensor unit including: mixing a conductive polymer with an absorbent to form a mixture; and then curing the mixture. The conductive polymer comprises 25-55 wt % of PAN and the absorbent comprises 45-75 wt % of PU based on 100 wt % of the solid constituent of the mixture.

According to a preferred embodiment of the present invention, the method of curing the mixture includes forming a film using the mixture under a thermal treatment.

According to a preferred embodiment of the present invention, the method of curing the mixture includes bake drying the mixture. Moreover, the conditions of bake drying the mixture include maintaining a constant temperature at a range between 50° C. to 70° C. for 280 min to 320 min.

According to a preferred embodiment of the present invention, the step of forming the mixture includes adding a solvent on mixing the conductive polymer and the absorbent, wherein the solvent includes toluene.

According to a preferred embodiment of the present invention, after forming the mixture and before curing the mixture, the mixture is coated onto a sensing circuit. The sensing circuit may comprise an alumina CLCC.

According to a preferred embodiment of the present invention, the gas sensor unit is used to detect a gas of alcohols by absorbing/desorbing the gas molecules of alcohols, which may change the resistance of the gas sensor unit. The measurement of change in the resistance of the gas sensor is indicative of presence of gas.

Since a conductive polymer material PAN is used as a sensing material, and PU is used together as an absorbent of the gas molecules in the present invention, and therefore the cost of the gas sensor can be effectively reduced and also the sensitivity of the gas sensor unit can be effectively promoted.

In order to make the aforementioned and other objects, features and advantages of the present invention comprehensible, preferred embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

The gas sensor unit according to the present invention mainly includes a conductive polymer and an absorbent for absorbing gas molecules. Furthermore, in a preferred embodiment of the present invention, the conductive polymer is PAN and the absorbent is PU. The concentration of the conductive polymer is 25-55 wt % and the concentration of the absorbent is 45-75 wt %, so that the gas sensor unit can have a preferred conductivity and film-forming mechanical property. In addition, the gas molecules that can be absorbed by the gas sensor unit includes molecules of alcohols, such as methanol and ethanol.

Since PAN is used as a sensing material in the gas sensor unit according to the present invention due to the conductivity, and PU is used together as an absorbent for absorbing gas molecules, and therefore the cost of the gas sensor can be effectively reduced and the sensitivity of the gas sensor can be effectively promoted. Moreover, the absorbent can absorb a gas from air, which would change chemical structure thereof and cause a change in the resistance of the gas sensor unit (PAN+PU) so that this change of resistance of the gas sensor unit, which can be measured in real time, is indicative of the presence of the gas.

Figure 1:
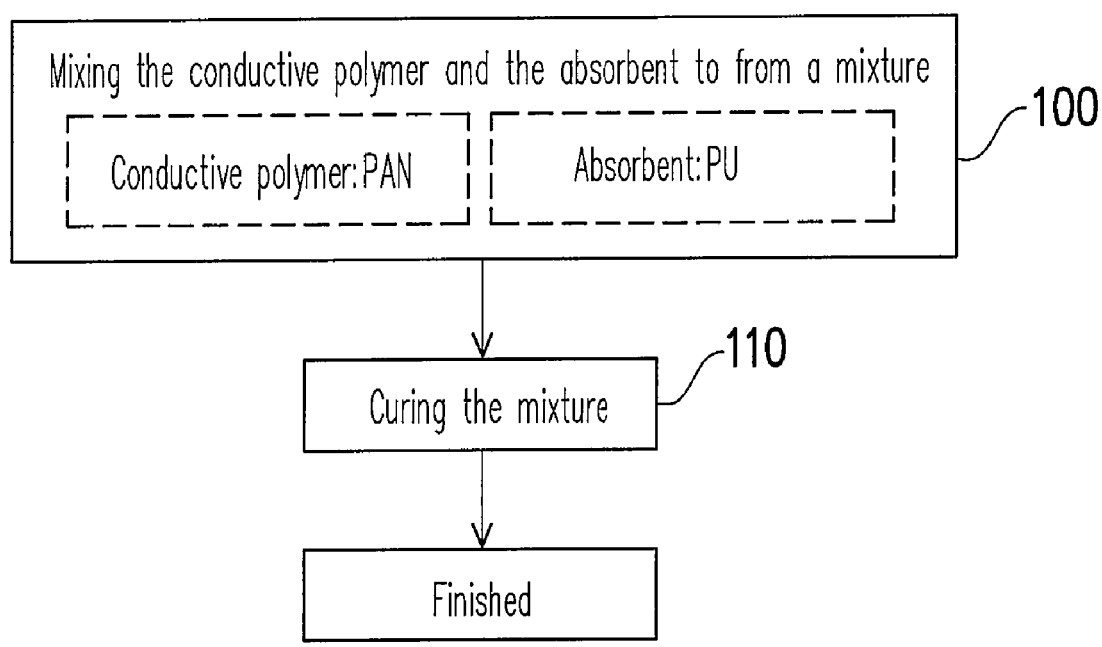
FIG. 1 is a flow chart of a process for forming a gas sensor unit according to a preferred embodiment of the present invention.

FIG. 1 is a flow chart of a process for forming a gas sensor unit according to another preferred embodiment of the present invention.

Referring to FIG. 1, in Step 100, the conductive polymer and the absorbent are mixed to form a mixture. The conductive polymer is PAN, and the absorbent is PU. The content of PAN is 25-55 wt % and the content of PU is 45-75 wt %. Furthermore, a solvent can be added to facilitate the mixing of the conductive polymer and the absorbent. For example, the solvent is toluene.

Next, in Step 110, the mixture is cured. The step of curing the mixture includes, for example, forming a film using the mixture under a thermal condition; or bake drying the mixture. The conditions of bake drying the mixture include, for example, maintaining a constant temperature at a range between 50 to 70° C. for 280 to 320 minutes. Thus, the fabrication of gas sensor unit is completed and can be used to detect alcohol gas by absorbing/desorbing the molecules of the alcohol gas, which cause a change in the resistance of the gas sensor unit accordingly.

In addition, between Step 100 and Step 110, the mixture may be selectively coated on a sensing circuit. The sensing circuit may comprise, e.g. an alumina CLCC. Several examples are listed below to illustrate the method of forming the gas sensor unit.

EXAMPLE 1

The Example 1 is directed to a gas sensor unit (PAN+PU) for measuring the electrical property (resistance), by detecting the DC resistance (impedance) variation sensitivity after twice continuous absorption/desorption experiment of methanol (MeOH). The starting material is 40 wt % of PAN and 60 wt % of PAN (NCO is 5.56%), and the sensing is carried out under the following experimental conditions: (1) semi-hermetic measurement system; (2) natural volatilization at normal temperature; and (3) a distance between the sensing surface of the gas sensor unit and the methanol liquid level of about 1.5 cm.

The method of fabricating the gas sensor unit according to the first example may be described as follows. Predetermined amounts of PU and PAN (in a viscous state) are blended. Next, an appropriate amount of solvent, for example toluene, is added, and then the mixture is stirred for 10 minutes to mix well. Next, the mixture is coated over a surface of an alumina CLCC without a pin. Next, the resulting structure is bake dried in an oven at a constant temperature of 60° C. for about 5 hr. Next, the resulting structure is removed from the oven and cooled. The gas sensor unit is used for absorption/desorption of methanol and then the DC impedance property is measured.

Figure 2:
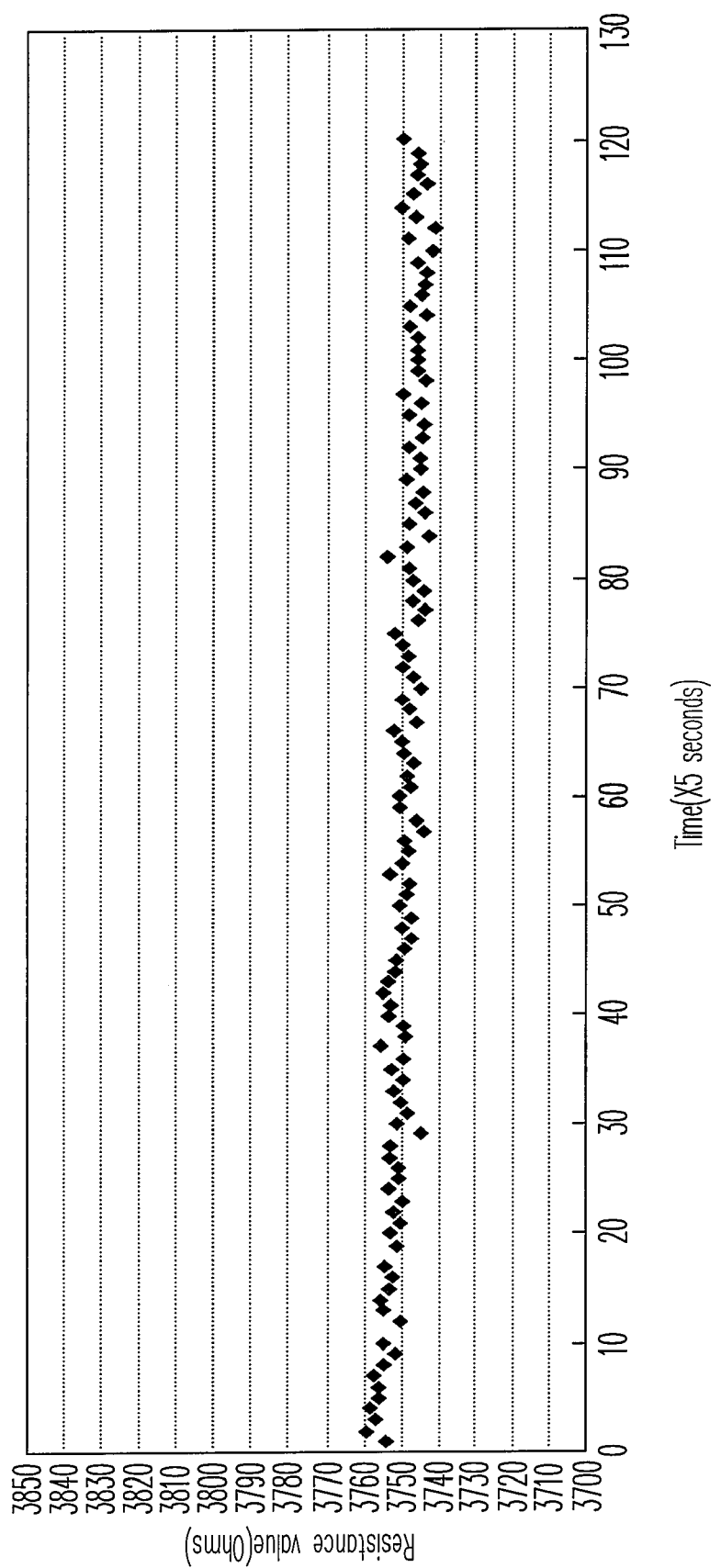
FIG. 2 is a curve diagram showing the relationship between the resistance value of a gas sensor unit (PAN/PU: 40/60 wt %) in a stand-by state and time according to a first embodiment of the present invention.

Referring to FIG. 2, a state of the gas sensor unit (PAN/PU: 40/60 wt %) according to the Example 1 measuring the DC impedance property in a stand-by state after cooling and before absorption/desorption of methanol is shown. The measured results show that the resistance value is also maintained between about 3740 Ohm and 3760 Ohm over time.

Figure 3:
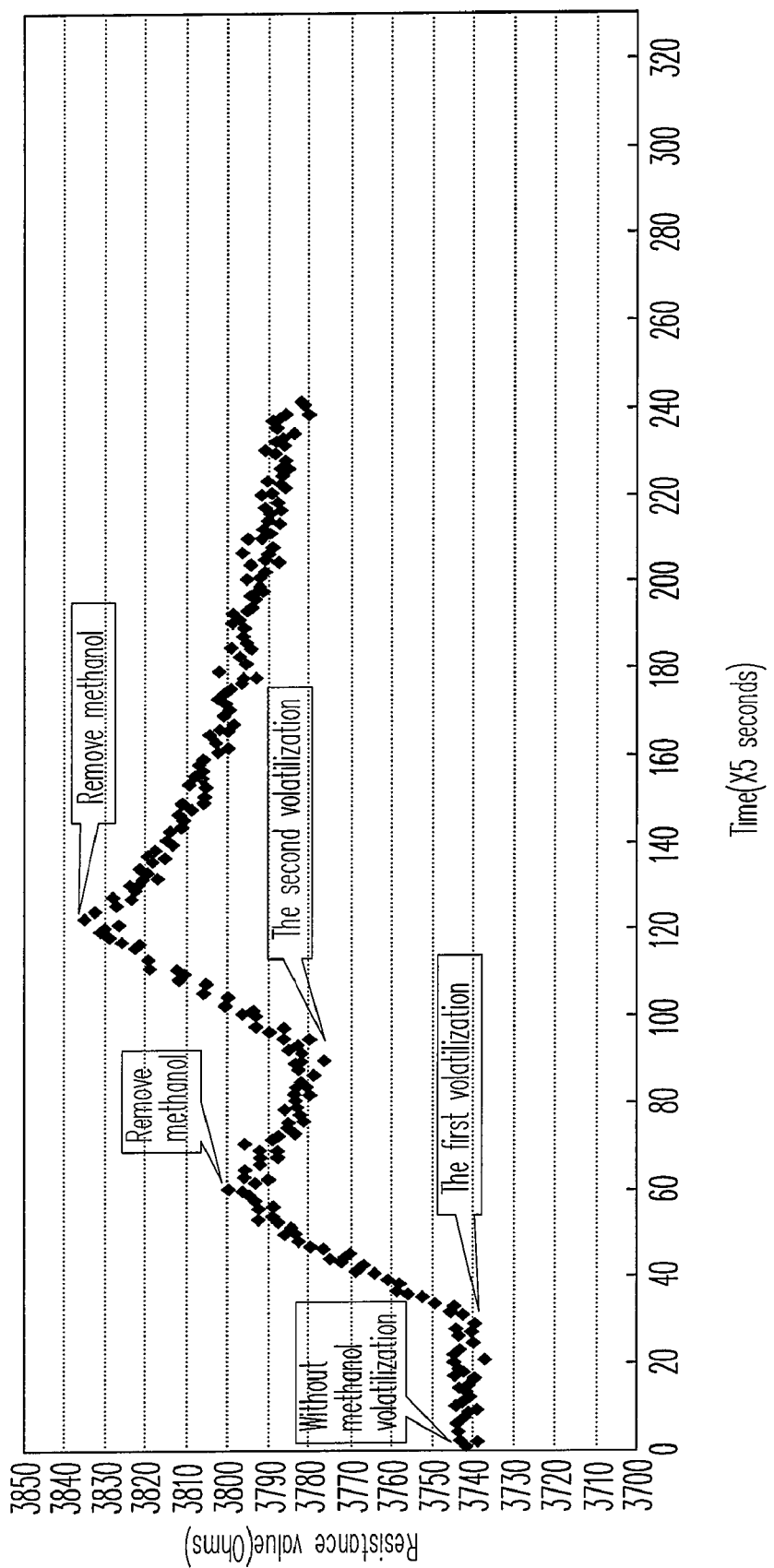
FIG. 3 is a curve diagram showing a relationship between resistance value of the gas sensor unit after sensing a gas and time according to the first embodiment of the present invention.

Next, after continuous absorption/desorption of methanol, the state of the gas sensor unit (PAN/PU: 40/60 wt %) according to the Example 1 measuring the DC impedance property after sensing a gas is shown in FIG. 3. The resistance value is maintained at a steady state all the time without methanol volatilization, while the resistance value is increased from 3740 Ohm to 3800 Ohm over time after a first volatilization of methanol. Next, the methanol solution is removed, and the resistance value is decreased thereupon. The resistance value is increased from 3775 Ohm to 3835 Ohm over time after a second volatilization. Next, the methanol solution is removed, and the resistance value is decreased thereupon.

That is to say, when the methanol volatilizes, gas sensor unit absorbs the methanol gas molecules, consequently the DC resistance of the gas sensor increases; and after the methanol is removed, the absorbed methanol molecules are desorbed from the gas sensor, consequently the DC resistance of the gas sensor decreases. Thus, a stable trend of impedance variation is exhibited, which is nearly linear and reproducible.

EXAMPLE 2

The gas sensor of Example 2 is similar to that of Example 1 except for 50 wt % of PAN and 50 wt % of PU are used as starting materials. A triple continuous absorption/desorption experiment of methanol (MeOH) is carried out, so as to detect the resistance (impedance) variation sensitivity.

Figure 4:
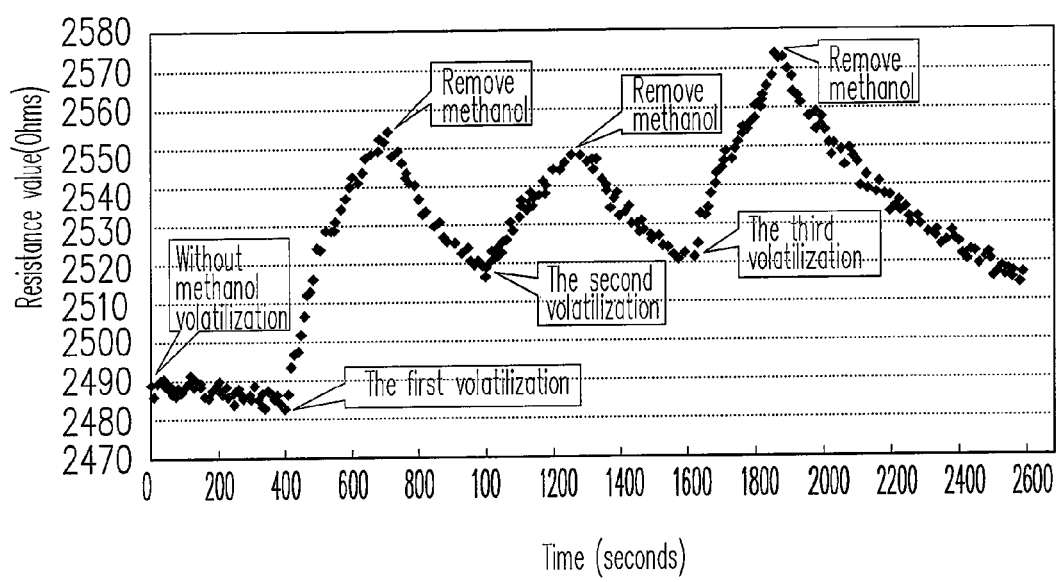
FIG. 4 is a curve diagram showing a relationship between resistance value of a gas sensor unit (PAN/PU: 50/50 wt %) after sensing the gas and time according to a second embodiment of the present invention.

Referring to FIG. 4, a state of the gas sensor unit (PAN/PU: 50/50 wt %) according to the Example 2 measuring the DC impedance property after sensing the gas is shown. The resistance value of the gas sensor is maintained at a steady state all the time without methanol volatilization, while the resistance value of the gas sensor is increased from 2485 Ohm to 2553 Ohm over time after a first volatilization of methanol. Next, the methanol solution is removed, and the resistance value of the gas sensor is decreased thereupon.

Next, after a second volatilization, the resistance value of the gas sensor is increased from 2516 Ohm to 2547 Ohm over time. And then, the methanol solution is removed, and the resistance value of the gas sensor is decreased thereupon.

Next, after a third volatilization of the methanol solution, the resistance value of the gas sensor is increased from 2519

Ohm to 2572 Ohm over time. Next, the methanol solution is removed, and the resistance value of the gas sensor is decreased thereupon.

Therefore, when the content of both PAN and PU is changed to 50 wt %, the DC resistance of the gas sensor is increased when the gas molecules of methanol are sensed; and after the methanol is removed, the DC resistance is decreased. In addition, regardless of the twice continuous absorption/desorption according to the Example 1 (as shown in FIG. 3) or the triple continuous absorption/desorption according to the Example 2 (as shown in FIG. 4), a stable trend of impedance variation is exhibited, which is nearly linear and is reproducible.

EXAMPLE 3

In the Example 3, 50 wt % of PAN and 50 wt % of PU are used as starting materials, and the twice continuous absorption/desorption experiment using ethanol is carried out to detect the resistance (impedance) variation sensitivity. The method of forming the gas sensor unit and the experimental conditions are similar to those of the Examples 1 and 2.

Figure 5:
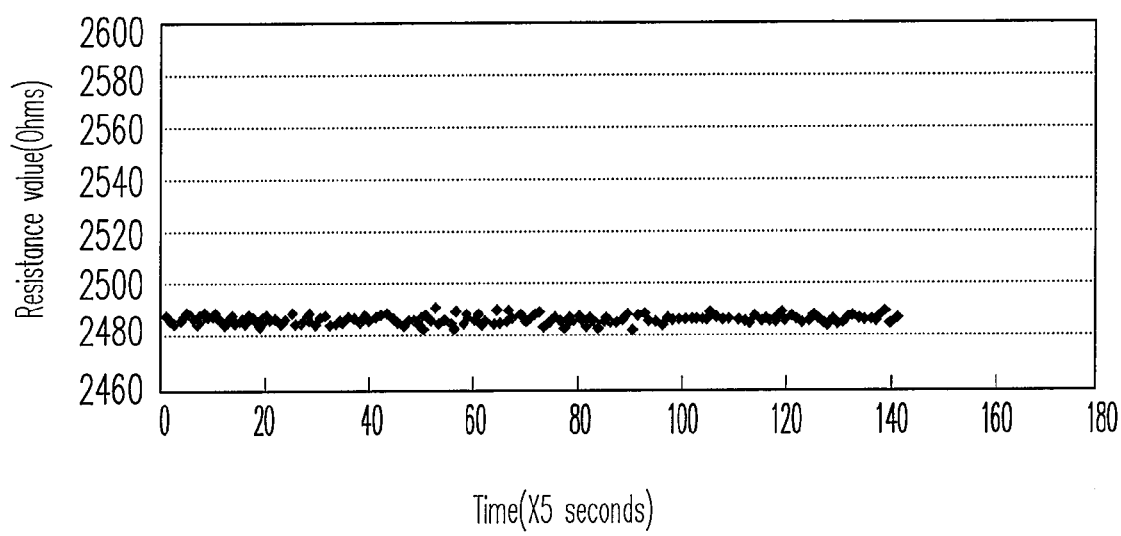
FIG. 5 is a curve diagram showing a relationship between resistance value of the gas sensor unit (PAN/PU: 50/50 wt %) in a stand-by state and time according to a third embodiment of the present invention.

Referring to FIG. 5, a state of the gas sensor unit (PAN/PU: 50/50 wt %) according to the Example 3 measuring the DC impedance property in a stand-by state after cooling and before the absorption/desorption of ethanol is shown. The measured results show that the resistance value is maintained between about 2485 Ohm and 2490 Ohm over time.

Figure 6:
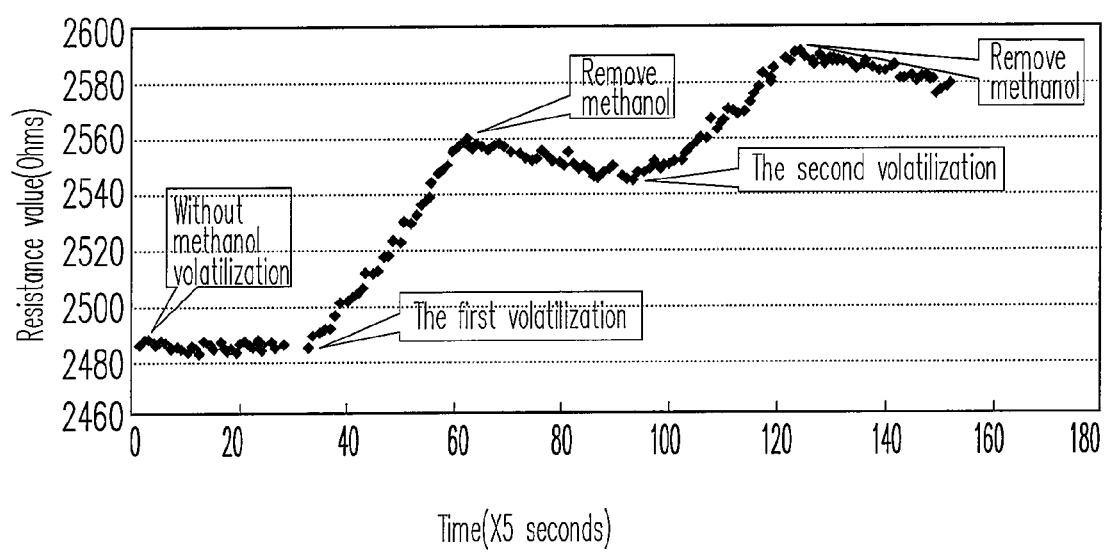
FIG. 6 is a curve diagram showing a relationship between resistance value of the gas sensor unit after sensing the gas and time according to the third embodiment of the present invention.

Next, after the continuous absorption/desorption of ethanol, a state of the gas sensor unit (PAN/PU: 50/50 wt %) according to the Example 3 after sensing the gas is as shown in FIG. 6. The resistance value of the gas sensor is maintained at a steady state without ethanol volatilization, while the resistance value of the gas sensor is increased from 2485 Ohm to 2560 Ohm over time after the first volatilization of ethanol. Next, the ethanol solution is removed, and the resistance value of the gas sensor is decreased thereupon. The resistance value of the gas sensor is increased from 2445 Ohm to 2583 Ohm over time after a second volatilization. Next, the ethanol solution is removed, and the resistance value of the gas sensor is decreased thereupon.

It is known that, after the gas sensor unit according to the Example 3 senses ethanol, the DC resistance is increased; and after the ethanol is removed, the DC resistance is decreased, thereby exhibiting a stable trend of impedance variation, which is nearly linear and reproducible.

As mentioned above, in the present invention, a low cost and highly sensitive "conductive" polymer material PAN with resistance property is used, and the polymer material PU with preferred mechanical property is used together with the PAN carrier to improve the mechanical property and as an absorbent for absorbing gas molecules. Accordingly, the gas sensor unit according to the present invention can be used for sensing a harmful gas in the air and issue a warning in real time. Moreover, according to the weight ratio range of the constituents in the gas sensor unit of the present invention, a preferred conductivity and film-forming mechanical property can be achieved.

While the present invention has been disclosed above by preferred embodiments, it is not intended to limit the scope of the invention. It will be apparent to those skilled in the art that various modifications and variations can be made to the present invention without departing from the scope or spirit of the invention. In view of the foregoing, it is intended that the present invention cover modifications and variations of this invention provided they fall within the scope of the following claims.

What is claimed is:

1. A gas sensor unit, comprising:
a conductive polymer, comprising 25-55 wt % polyaniline (PAN) of the total weight of the gas sensor unit; and
an absorbent, for absorbing gas molecules, comprising 45-75 wt % polyurethane (PU) of the total weight of the gas sensor unit.

2. The gas sensor unit as claimed in claim 1, wherein the gas molecules absorbed comprises molecules of alcohols.

3. The gas sensor unit as claimed in claim 2, wherein the molecules of alcohols comprises methanol molecules.

4. The gas sensor unit as claimed in claim 2, wherein the molecules of alcohols comprises ethanol molecules.

5. The gas sensor unit as claimed in claim 1, further comprising a sensing circuit for sensing the resistance of the gas sensor unit.

6. The gas sensor unit as claimed in claim 5, wherein the sensing circuit comprises an alumina ceramic leaded chip carrier (CLCC).

7. The gas sensor unit as claimed in claim 1, wherein gas sensor unit is used for absorbing/desorbing the gas molecules of alcohols, a change in the resistance of the gas sensor unit is a measure of presence or absence of the gas molecules of the alcohols.

8. A method of fabricating a gas sensor unit, comprising:
mixing a conductive polymer with an absorbent to form a mixture, wherein the mixture comprises 25-55 wt % conductive polymer and 45-75 wt % absorbent based on 100 wt % of a solid constituent of the mixture, and wherein the conductive polymer comprises polyaniline (PAN) and the absorbent comprises polyurethane (PU); and
curing the mixture.

9. The method of forming the gas sensor unit as claimed in claim 8, wherein the step of curing the mixture comprises forming a film and thermally treating the film.

10. The method of forming the gas sensor unit as claimed in claim 8, wherein the step of curing the mixture comprises bake drying the mixture.

11. The method of forming the gas sensor unit as claimed in claim 10, wherein the condition of bake drying the mixture is carried out under a temperature range from 50° C. to 70° C. for 280-320 minutes.

12. The method of forming the gas sensor unit as claimed in claim 8, wherein the step of forming the mixture comprises adding a solvent when mixing the conductive polymer and the absorbent.

13. The method of forming the gas sensor unit as claimed in claim 12, wherein the solvent comprises toluene.

14. The method of forming a gas sensor unit as claimed in claim 8, further comprising a step of coating the mixture on a sensing circuit before curing the mixture, wherein the resistance variation of the gas sensor unit is a measure of presence or absence of gas.

15. The method of forming the gas sensor unit as claimed in claim 14, wherein the sensing circuit comprises an alumina ceramic leaded chip carrier (CLCC).

* * * * *